United States Patent [19]

Wu

[11] Patent Number: 5,237,118
[45] Date of Patent: Aug. 17, 1993

US005237118A

[54] ETHYLENE OLIGOMERIZATION

[75] Inventor: An-hsiang Wu, Bartlesville, Okla.

[73] Assignee: Phillips Petroleum Company, Bartlesville, Okla.

[21] Appl. No.: 933,146

[22] Filed: Aug. 21, 1992

[51] Int. Cl.$^5$ .......................... C07C 2/26; C07C 2/34; C07C 2/24

[52] U.S. Cl. .................................. 585/511; 585/514; 585/312; 585/313

[58] Field of Search ................ 585/511, 514, 312, 313

[56] References Cited

U.S. PATENT DOCUMENTS

| | | | |
|---|---|---|---|
| 4,482,640 | 11/1984 | Knudsen et al. | 502/155 |
| 4,487,847 | 12/1984 | Knudsen | 502/155 |
| 4,518,814 | 5/1985 | Knudsen et al. | 585/523 |
| 4,528,415 | 7/1985 | Knudsen | 585/527 |

Primary Examiner—Patrick P. Garvin
Assistant Examiner—E. D. Irzinski
Attorney, Agent, or Firm—Carl D. Corvin

[57] ABSTRACT

An ethylene oligomerization process comprising: (a) contacting, in a reaction solution, an organonickel compound and a phosphine compound to form a first reaction mixture; and thereafter (b) contacting said first reaction mixture with ethylene to form a second reaction mixture; and concurrently with step (b) or thereafter, contacting said second reaction mixture with a fluorinated organoacid; while maintaining a reaction temperature from about 0° C. to about 200° C., and a reaction pressure of about 1 to about 10,000 psig.

21 Claims, No Drawings

ETHYLENE OLIGOMERIZATION

BACKGROUND OF THE INVENTION

This invention relates to the field of ethylene oligomerization.

A variety of catalysts, both homogeneous and heterogeneous, have been disclosed as oligomerization catalysts for ethylene. For example, U.S. Pat. No. 4,482,640 and U.S. Pat. No. 4,487,847 disclose ethylene oligomerization and ethylene dimerization catalysts and processes. Efforts to raise the productivity and selectivity of oligomerization catalysts and processes is ongoing due to the increasing importance of molecules with a molecular weight greater than ethylene.

SUMMARY OF THE INVENTION

It is an object of this invention to provide an improved ethylene oligomerization process.

In accordance with this invention, an ethylene oligomerization process is provided, comprising, consisting essentially of, or consisting of: (a) contacting, in a reaction solution, an organonickel compound and a phosphine compound to form a first reaction mixture; and thereafter (b) thoroughly contacting said first reaction mixture with ethylene to form a second reaction mixture; and concurrently with step (b) or thereafter, contacting said reaction mixture with a fluorinated organoacid; while maintaining a reaction temperature from about 0° C. to about 200° C., and a reaction pressure of about 1 to about 10,000 psig.

This invention can suitably be practiced in absence of any reactants, conditions, or parameters not specifically mentioned herein.

DETAILED DESCRIPTION OF THE INVENTION

In general, the oligomerization system of the invention comprises the following components: an organonickel compound, a phosphine compound, a fluorinated organoacid compound, a reaction solution, and ethylene. These compounds must be contacted in a particular order to realize the benefits of this invention.

The characteristics of these compounds are as follows. The nickel component of the organonickel compound should already be in the zero valence state or it should be able to undergo reduction to the zero valence state. The organic component should be an unsaturated group. Suitable examples of organonickel compounds include, but are not limited to, bis(1,5-cyclooctadiene)nickel, bis(tricyclohexylphosphine)nickel, nickel tetracarbonyl, (cyclododecatriene)nickel, bis(ethylene)(dicyclohexylphosphine)nickel, tetrakis(triphenylphosphine)nickel, and bis(triphenylphosphine)nickel dicarbonyl. Bis(1,5-cyclooctadiene)nickel is particularly preferred. Additionally, mixtures of two or more organonickel compounds are within the scope of this invention.

The phosphine compound has a general formula $PR_3$, wherein R is independently selected from the group consisting of hydrogen and hydrocarbyl radicals, provided that the hydrocarbyl radical has 1 to about 20 carbon atoms, and that any alkenyl substitution be at least 3 carbon atoms removed from the phosphorus atom and at least one R is not hydrogen. Suitable examples of phosphine compounds include, but are not limited to, dicyclohexylphosphine, tricyclohexylphosphine, triethylphosphine, tributylphosphine, diethylphenylphosphine, dicyclohexylphenylphosphine, tribenzylphosphine, ortho-tolyldiphenylphosphine, di(ortho-tolyl)phenylphosphine, triisopropylphosphine, triisobutylphosphine, tritertbutylphosphine, phenylphosphine, diphenylphosphine, and triphenylphosphine. The most preferred compounds are dicyclohexylphosphine and tricyclohexylphosphine. Additionally, mixtures of two or more phosphine compounds are within the scope of this invention.

The molar ratio of the phosphine compound to nickel is from about 0.01 to about 100. Increasing the molar ratio above one decreases productivity and increases selectivity. Therefore, a molar ratio of about 0.1 to about 10 is preferred and a molar ratio of 0.5 to 5 is most preferred.

The preferred fluorinated organoacid is a fluorinated carboxylic acid of the formula R"COOH wherein R" represents a $C_1$ to about $C_{10}$ fluorinated hydrocarbyl radical having at least one fluorine (F) atom. Suitable fluorinated carboxylic acids include, but are not limited to, trifluoroacetic acid, heptafluorobutyric acid, difluoroacetic acid, pentafluoropropionic acid and perfluoroadipic acid. Additionally, mixtures of two or more of these acids is within the scope of this invention. The preferred fluorinated carboxylic acid is trifluoroacetic acid. Fluorinated organoacids also within the scope of certain broad aspects of the invention are fluorinated sulfonic acids such as trifluoromethanesulfonic acid and heptafluoroethanesulfonic acid.

The molar ratio of fluorinated organoacid compound to nickel is from about 0.01 to about 1000. Preferably, the molar ratio is from about 0.1 to about 100, and most preferably 0.5 to 50.

The reaction solution should be an aromatic hydrocarbon, a fluorinated aromatic hydrocarbon, a primary alcohol, a secondary alcohol, a tertiary alcohol, or a fluorinated primary, secondary, or tertiary alcohol. Suitable examples include, but are not limited to, toluene, ethanol, 2-butanol, 2-methyl-1-propanol, 2-pentanol, fluorobenzene, hexanol, octanol, and 2-ethyl-1-butanol. Additionally, mixtures of two or more of these reaction solutions is within the scope of this invention.

The ethylene used in this oligomerization is preferably substantially pure. That is, it should be polymerization grade ethylene. The molar ratio of ethylene to nickel should be about 1 to about 100,000,000, preferably about 1 to about 50,000,000 and most preferably 1 to 10,000,000.

The reaction temperature is from about 0° C. to about 200° C. However, while increasing the temperature increases the productivity, it also decreases the selectivity. Therefore, a reaction temperature of about 20° C. to about 120° C. is preferred, while a temperature of 40° C. to 100° C. is most preferred.

The reaction pressure is from about 1 to about 10,000 psig. However, while increasing the pressure increases the productivity, when the reaction solution is an alcohol, it also decreases the selectivity to dimers of ethylene. Additionally, for aromatics a maximum productivity pressure is reached around 700 psig. Therefore, when the reaction solution is an alcohol, a pressure of about 100 psig to about 8,000 psig is preferred, while a pressure of 200 to 5,000 psig is most preferred. However, when the reaction solution is an aromatic, a pressure of about 400 to about 1,000 psig is preferred, while a pressure of 500 to 900 is most preferred. The reaction time is from about 1 minute to about 100 hours, preferably about 10 minutes to about 1,000 minutes, and most preferably 30 minutes to 300 minutes.

It is essential to this invention that the organonickel compound and the phosphine compound be contacted together first in a reaction solution. This contacting of the organonickel compound and the phosphine compound will form a reaction mixture. Thereafter, this reaction mixture is thoroughly contacting with ethylene. Thereafter, or concurrently with the thorough contacting of the reaction mixture with the ethylene, the fluorinated organoacid compound can be contacted with the reaction mixture. This process is accomplished while maintaining a reaction temperature and reaction pressure as described above.

EXAMPLES

These examples are provided to further assist a person skilled in the art with understanding this invention. The particular reactants, conditions, and the like, are intended to be generally illustrative of this invention and are not meant to be construed as unduly limiting the reasonable scope of this invention.

All runs described in these examples were carried out in a 300 milliliter stainless steel (316-SS) Autoclave Engineers stirred tank reactor. The following chemicals were commercially available and used as received:
(1) bis(1,5-cyclooctadiene) nickel(0), hereafter referred to as Ni(COD)$_2$;
(2) dicyclohexylphosphine, hereafter referred to as DCHP;
(3) tricyclohexylphosphine, hereafter refer to as TCHP;
(4) trifluoroacetic acid, hereafter referred to as TFAA;
(5) ethanol;
(6) 2-butanol;
(7) 2-methyl-1-propanol;
(8) 2-pentanol;
(9) hexanol;
(10) octanol;
(11) 2,2,2 trifluoroethanol;
(12) 2-ethyl-1-butanol;
(13) 2-methyl-1-butanol; and
(14) decanol.

The following chemicals were distilled from a sodium meta-benzophenone solution prior to use:
(1) toluene;
(2) fluorobenzene; and
(3) trifluoromethylbenzene.

Product analysis was performed with an HP 5890 II gas chromatograph using a capillary DB-1 (60 m) column. The temperature profile was set for 30° C. initially with a 15° C. per minute increase in the temperature until a temperature of 285° C. was reached. This final temperature was then held for 13 minutes. Detection was accomplished with a flame ionization detector in the area percent mode. Selectivity of 1-olefins and the weight percent distributions were determined by this method. Catalyst productivity is defined as the oligomerized products (i.e. C$_4$ and higher) produced per gram of nickel per hour. This was determined by the totalizer readings on the ethylene flow meter. All olefins were identified by comparison with commercially obtained samples.

EXAMPLE I

This example illustrates a prior art method of ethylene oligomerization. In general, it comprises adding a nickel compound, a phosphine compound, and an acid compound to the reactor followed by the addition of ethylene to the reactor.

The reactor was first purged with nitrogen gas to remove any residual air. This was followed by the addition of the following compounds to the reactor:
(1) 50 milliliters of reaction solution as listed below in Table I;
(2) 0.198 grams (1.0 millimoles) of DCHP; and
(3) 0.275 grams (1.0 millimoles) of Ni(COD)$_2$;
(4) 0.114 grams (1.0 millimoles) of TFAA.

The reactor was then sealed. After the reactor was sealed, it was purged with ethylene to remove the nitrogen gas. The reactor was then pressurized to a pressure of 700 pounds per square inch gauge with ethylene. The contents of the reactor were then agitated for about five minutes. The reaction time was 60 minutes and the reaction temperature was 40° C.

The results are presented below in Table I.

TABLE I

| Run | Reaction Solution[1] | Productivity[2] | Amount of C$_4$H$_8$[3] | Amount of 1-C$_{10}$H$_{20}$[4] |
|---|---|---|---|---|
| 11 | Toluene | 1360 | 23 | 69 |
| 12 | Ethanol | 290 | 72 | 77 |
| 13 | 2-Butanol | 210 | 54 | 84 |
| 14 | 2-Methyl-1-Propanol | 260 | 70 | 67 |
| 15 | 2-Pentanol | 700 | 43 | 90 |

[1] The term reaction solution is not meant to be construed as an inert or unreactive medium in which the ethylene oligomerization takes place. The reaction solution is considered to be a necessary participant in the ethylene oligomerization.
[2] The productivity is expressed in grams of oligomerized product produced per gram of nickel used per hour.
[3] The amount of C$_4$H$_8$ produced is expressed as a weight percent. It is determined by taking the total weight of all C$_4$H$_8$ products and dividing by the total weight of all of the ethylene oligomerization products.
[4] The amount of 1-C$_{10}$H$_{20}$ produced is expressed as a weight percent. It is determined by taking the total weight of 1-C$_{10}$H$_{20}$ produced and dividing by the total weight of all C$_{10}$H$_{20}$ products produced.

EXAMPLE II

This example illustrates an embodiment of the invention. In general, it comprises adding a nickel compound and a phosphine compound to the reactor followed by the addition of ethylene to the reactor. The acid compound is added to the reactor after the addition of ethylene to the reactor.

The reactor was first purged with nitrogen gas to remove any residual air. This was followed by the addition of the following compounds to the reactor:
(1) 48 milliliters of the reaction solution as listed below;
(2) 0.198 grams (1.0 millimoles) of DCHP; and
(3) 0.275 grams (1.0 millimoles) of Ni(COD)$_2$.

The reactor was then sealed. After the reactor was sealed, it was purged with ethylene to remove the nitrogen gas. The reactor was then pressurized to a pressure of 50 pounds per square inch gauge with ethylene. The contents of the reactor was then agitated for about five minutes.

After this agitation, 0.114 grams (1.0 millimoles) of TFAA, in 2 ml of a solution with the appropriate solvent as disclosed below, was then added to a second vessel. Thereafter, the second vessel's pressure was increased to 700 pounds per square inch gauge with ethylene. The contents of this second vessel were then added to the reactor. The reactor's pressure was then increased to 700 pounds per square inch gauge with ethylene. The reaction time and temperature were the same as in Example I.

The results are disclosed in Table II below.

TABLE II

| Run | Reaction Solution[1] | Productivity[2] | Amount of $C_4H_{10}$[3] | Amount of $1$-$C_{10}H_{20}$[4] |
|---|---|---|---|---|
| 21 | Toluene | 1232 | 36 | 78 |
| 22 | Ethanol | 1100 | 71 | 89 |
| 23 | 2-Butanol | 527 | 38 | 93 |
| 24 | 2-Methyl-1-Propanol | 1017 | 56 | 95 |
| 25 | 2-Pentanol | 495 | 34 | 97 |

[1] See Note 1, Table I.
[2] See Note 2, Table I.
[3] See Note 3, Table I.

Comparing the results in Table II with the prior art results in Table I, it is apparent that except for when the reaction solution was toluene or 2-pentanol, the productivity was increased by using the invention. Furthermore, it is apparent that the selectivity was also increased by using the invention.

The results also show that high catalyst productivity (i.e. over 1000 grams of oligomerized products produced per gram of nickel used per hour) was obtained when the reaction solution was either toluene, ethanol, or 2-methyl-1-propanol. Additionally, when alcohol was used as the reaction solution, higher selectivity to 1-olefins was discovered. Furthermore, when the reaction solution was ethanol, higher production of dimerization product was discovered.

EXAMPLE III

This example illustrates another embodiment of the invention. In particular, it describes the effect of pressure on ethylene oligomerization.

TABLE III

| Run[1] | Reaction Solution[2] | Pressure[3] | Productivity[4] | Amount $1$-$C_{10}H_{20}$[5] | Amount of Cx Produced[6] | | | | | |
|---|---|---|---|---|---|---|---|---|---|---|
| | | | | | $C_4$ | $C_6$ | $C_8$ | $C_{10}$ | $C_{12}$ | $C_{14}$ + Up |
| 31A | Toluene | 300 | 230 | 75 | 78 | 14 | 4 | 3 | 1 | 0 |
| 31B | Toluene | 500 | 516 | 78 | 75 | 15 | 4 | 3 | 2 | 1 |
| 31C | Toluene | 700 | 757 | 80 | 42 | 23 | 15 | 10 | 6 | 4 |
| 31D | Toluene | 900 | 466 | 90 | 80 | 15 | 3 | 1 | 1 | 0 |
| 32A | Fluorobenzene | 300 | 610 | 74 | 72 | 16 | 6 | 3 | 2 | 1 |
| 32B | Fluorobenzene | 500 | 1681 | 80 | 70 | 18 | 6 | 3 | 2 | 1 |
| 32C | Fluorobenzene | 700 | 2580 | 81 | 32 | 31 | 17 | 10 | 6 | 4 |
| 32D | Fluorobenzene | 900 | 1328 | 89 | 76 | 17 | 4 | 2 | 1 | 0 |
| 33A | 2-Pentanol | 300 | 303 | 92 | 55 | 29 | 11 | 4 | 1 | 0 |
| 33B | 2-Pentanol | 500 | 407 | 93 | 45 | 28 | 18 | 6 | 2 | 1 |
| 33C | 2-Pentanol | 700 | 495 | 97 | 34 | 32 | 19 | 9 | 4 | 2 |
| 33D | 2-Pentanol | 900 | 715 | 99 | 26 | 28 | 23 | 13 | 7 | 3 |
| 34A | Hexanol | 300 | 208 | 94 | 70 | 23 | 5 | 2 | 0 | 0 |
| 34B | Hexanol | 500 | 213 | 96 | 64 | 26 | 6 | 3 | 1 | 0 |
| 34C | Hexanol | 700 | 246 | 99 | 59 | 29 | 9 | 2 | 1 | 0 |
| 34D | Hexanol | 900 | 603 | 99 | 40 | 32 | 17 | 7 | 3 | 1 |
| 35A | 2-Butanol | 300 | 376 | 84 | 52 | 24 | 16 | 6 | 2 | 0 |
| 35B | 2-Butanol | 500 | 438 | 87 | 44 | 28 | 17 | 7 | 3 | 1 |
| 35C | 2-Butanol | 700 | 527 | 93 | 38 | 30 | 19 | 8 | 4 | 1 |
| 35D | 2-Butanol | 900 | 847 | 95 | 27 | 29 | 23 | 12 | 6 | 3 |

[1] All runs were conducted according to the procedure disclosed in Example II. The temperature the oligomerization was conducted at was 40° C. Other compounds used in the oligomerization were Ni(COD)$_2$, DCHP, and TFAA the amounts used were the same as Example II. The reaction time was 60 minutes.
[2] See Note 1, Table I.
[3] The pressure is expressed in pounds per square inch gauge (hereafter referred to as psig).
[4] See Note 2, Table I.
[5] See Note 4, Table I.
[6] The amount of $C_x$ produced is expressed as a weight percent. It is determined by taking the total weight of $C_x$ (X = 4, 6, 8, 10, 12, or 14 + up) and dividing by the total weight of all oligomerized products produced.

The results in Table III shows that for aromatic compounds a pressure between 500 and 900 psig is best. The results in Table III also shows that for alcohols, higher pressures (>700 psig) produced higher productivities. Additionally, regardless of the reaction solution used, the amount of 1-$C_{10}H_{20}$ produced increased.

EXAMPLE IV

This example illustrates another embodiment of the invention. In particular, it describes the effect of temperature on ethylene oligomerization.

TABLE IV

| Run[1] | Reaction Solution[2] | Reaction Temp.[3] | Productivity[4] | Amount of $1$-$C_{10}H_{20}$[5] | Amount of Cx Produced[6] | | | | | |
|---|---|---|---|---|---|---|---|---|---|---|
| | | | | | $C_4$ | $C_6$ | $C_8$ | $C_{10}$ | $C_{12}$ | $C_{14}$ + Up |
| 41A | 2-Pentanol | 30 | 180 | 98 | 64 | 25 | 9 | 3 | 1 | 0 |
| 41B | 2-Pentanol | 40 | 495 | 97 | 34 | 32 | 19 | 9 | 4 | |
| 41C | 2-Pentanol | 50 | 1021 | 92 | 32 | 28 | 18 | 12 | 6 | 4 |
| 41D | 2-Pentanol | 60 | 1240 | 90 | 30 | 27 | 20 | 14 | 6 | 3 |
| 42A | Octanol | 30 | 161 | 99 | 76 | 19 | 3 | 2 | 0 | 0 |
| 42B | Octanol | 40 | 246 | 99 | 59 | 29 | 9 | 2 | 1 | 0 |
| 42C | Octanol | 50 | 657 | 94 | 45 | 28 | 16 | 7 | 3 | 1 |

TABLE IV-continued

| Run[1] | Reaction Solution[2] | Reaction Temp.[3] | Productivity[4] | Amount of 1-$C_{10}H_{20}$[5] | $C_4$ | $C_6$ | $C_8$ | $C_{10}$ | $C_{12}$ | $C_{14}$ + Up |
|---|---|---|---|---|---|---|---|---|---|---|
| 42D | Octanol | 60 | 939 | 90 | 40 | 27 | 18 | 9 | 4 | 2 |

[1] All runs were conducted according to the procedure disclosed in Example II. The reaction was carried out under 700 psig ethylene. Other compounds used in the oligomerization were Ni(COD)$_2$, DCHP, and TFAA the amounts used were the same as Example II. The reaction time was 60 minutes.
[2] See Note 1, Table I.
[3] The reaction temperature is expressed in degrees Celsius.
[4] See Note 2, Table I.
[5] See Note 4, Table I.
[6] See Note 6, Table III.

The results in Table IV shows that increasing the temperature increased the productivity, but decreased the amount of 1-$C_{10}H_{20}$ produced, and the amount of $C_4$ produced. However, increasing the reaction temperature increased the amount of $C_6$ and higher produced.

EXAMPLE V

This example illustrates another embodiment of the invention. In particular, it describes the effect of reaction time on ethylene oligomerization.

The results in Table V shows that the reaction time had only a slight decreasing affect on the formation of 1-$C_{10}H_{20}$. However, there was an increase in the amount of $C_6$ product formed.

EXAMPLE VI

This example illustrates another embodiment of the invention. In particular, it describes the effect of the molar equivalent amount of phosphines on ethylene oligomerization.

TABLE V

| Run[1] | Reaction Solution[2] | Reaction Time[3] | Amount of 1-$C_{10}H_{20}$[4] | $C_4$ | $C_6$ | $C_8$ | $C_{10}$ | $C_{12}$ | $C_{14}$ + Up |
|---|---|---|---|---|---|---|---|---|---|
| 51A | 2-Pentanol | 60 | 98 | 46 | 31 | 15 | 6 | 2 | 0 |
| 51B | 2-Pentanol | 120 | 97 | 42 | 31 | 16 | 7 | 3 | 1 |
| 51C | 2-Pentanol | 180 | 97 | 34 | 32 | 19 | 9 | 4 | 2 |
| 51D | 2-Pentanol | 240 | 96 | 33 | 30 | 21 | 10 | 4 | 2 |
| 51E | 2-Pentanol | 300 | 96 | 32 | 29 | 20 | 11 | 6 | 2 |
| 52A | Octanol | 60 | 99 | 64 | 26 | 8 | 2 | 0 | 0 |
| 52B | Octanol | 120 | 99 | 61 | 28 | 8 | 2 | 1 | 0 |
| 52C | Octanol | 180 | 99 | 59 | 29 | 9 | 2 | 1 | 0 |
| 52D | Octanol | 240 | 98 | 55 | 30 | 11 | 3 | 1 | 0 |
| 52E | Octanol | 300 | 97 | 53 | 30 | 12 | 4 | 1 | 0 |
| 52F | Octanol | 360 | 96 | 52 | 30 | 13 | 4 | 1 | 0 |

[1] All runs were conducted according to the procedures disclosed in Example II. The reaction was carried out under 700 psig ethylene. Other compounds used in the oligomerization were Ni(COD)$_2$, DCHP, and TFAA. The reaction temperature was 40° C.
[2] See Note 1, Table I.
[3] The reaction time is expressed in minutes.
[4] See Note 4, Table I.
[5] See Note 6, Table III.

TABLE VI-A

| Run[1] | Phosphine | Molar Ratio of Phosphine to Nickel[2] | Reaction Solution[3] | Reaction Temperature[4] | Reaction Time[5] | Reaction Pressure[6] | Productivity[7] | Amount of $C_4H_6$[8] | Amount of 1-$C_{10}H_{20}$[9] |
|---|---|---|---|---|---|---|---|---|---|
| 6A1A | DCHP | 1 | TFMB[10] | 34 | 60 | 800 | 1516 | 32 | 68 |
| 6A1B | DCHP | 2 | TFMB | 37 | 60 | 800 | 1208 | 34 | 74 |
| 6A1C | DCHP | 3 | TFMB | 36 | 60 | 800 | 962 | 37 | 83 |
| 6A1D | DCHP | 4 | TFMB | 35 | 60 | 800 | 793 | 38 | 87 |
| 6A1E | DCHP | 5 | TFMB | 37 | 60 | 800 | 762 | 36 | 92 |
| 6A2A | TCHP | 1 | Toluene | 49 | 60 | 700 | 1546 | 25 | 78 |
| 6A2B | TCHP | 2 | Toluene | 47 | 60 | 700 | 1024 | 26 | 81 |
| 6A2C | TCHP | 3 | Toluene | 44 | 60 | 700 | 736 | 25 | 87 |
| 6A2D | TCHP | 4 | Toluene | 43 | 60 | 700 | 521 | 25 | 90 |
| 6A2E | TCHP | 5 | Toluene | 43 | 60 | 700 | 500 | 25 | 91 |
| 6A3A | TCHP | 1 | Fluorobenzene | 40 | 60 | 700 | 2898 | 35 | 78 |
| 6A3B | TCHP | 2 | Fluorobenzene | 40 | 60 | 700 | 1844 | 36 | 81 |
| 6A3C | TCHP | 3 | Fluorobenzene | 40 | 60 | 700 | 1526 | 35 | 84 |
| 6A3D | TCHP | 4 | Fluorobenzene | 40 | 60 | 700 | 1337 | 34 | 88 |
| 6A3E | TCHP | 5 | Fluorobenzene | 40 | 60 | 700 | 1185 | 36 | 90 |

[1] All runs were conducted according to the procedure disclosed in Example II. Other compounds used in the oligomerization were Ni(COD)$_2$ and TFAA the amounts used were the same as Example II.
[2] The molar ratio of phosphine to nickel was determined by dividing the number of molar equivalents of phosphine by the number of moles of nickel.
[3] See Note 1, Table I.
[4] See Note 3, Table IV.
[5] See Note 3, Table V.
[6] See Note 2, Table I.
[8] See Note 3, Table I.
[9] See Note 4, Table I.
[10] Trifluoromethylbenzene.

TABLE VI-B

| Run[1] | Phosphine | Molar Ratio[2] of Phosphine to Nickel | Productivity[3] | Amount of $C_4H_8$[4] | Amount of 1-$C_4H_8$[5] |
|---|---|---|---|---|---|
| 6B1A | DCHP | 1 | 27500 | 90 | 3 |
| 6B1B | DCHP | 2 | 18450 | 91 | 72 |
| 6B1C | DCHP | 3 | 7658 | 90 | 95 |
| 6B1D | DCHP | 4 | 3570 | 88 | 99 |
| 6B2A | TCHP | 1 | 20580 | 95 | 10 |
| 6B2B | TCHP | 2 | 12247 | 88 | 68 |
| 6B2C | TCHP | 3 | 2710 | 91 | 96 |
| 6B2D | TCHP | 4 | 2110 | 97 | 100 |
| 6B3A | DCHP + TCHP[6] | 2 | 13480 | 93 | 82 |
| 6B3B | DCHP + TCHP[7] | 3 | 4942 | 91 | 90 |
| 6B3C | DCHP + TCHP[8] | 3 | 4490 | 92 | 95 |
| 6B3D | DCHP + TCHP[9] | 4 | 2170 | 93 | 100 |

[1] All runs were conducted according to the procedure disclosed in Example II. The temperature the oligomerization was conducted at was 40° C. Each run was conducted for 60 minutes. The reaction was carried out under 700 psig ethylene. Other compounds used in the oligomerization were Ni(COD)$_2$, TFAA (in a one molar equivalent ratio with Ni(COD)$_2$), and 2,2,2-trifluoroethanol.
[2] See Note 2, Table VIA.
[3] See Note 2, Table I.
[4] See Note 3, Table I.
[5] The amount of 1-$C_4H_8$ produced, dividing by the total weight of all $C_4H_8$ products produced.
[6] In a molar ratio of 1:1.
[7] In a molar ratio of 1:2.
[8] In a molar ratio of 2:1.
[9] In a molar ratio of 2:2.

This data shows that increasing the molar ratio of phosphine to nickel decreased the productivity, and increased the selectivity to 1-$C_4H_8$.

EXAMPLE VII

This example illustrates another embodiment of the invention. In particular, it describes the effect of the amount of acids on ethylene oligomerization.

TABLE VII-A

| Run[1] | Molar Ratio of TFAA to Nickel[2] | Reaction Temp.[3] | Reaction Time[4] | Productivity[5] | Amount of $CrH_8$[6] | Amount of 1-$C_{10}H_{20}$[7] |
|---|---|---|---|---|---|---|
| 7A1 | 1 | 37 | 120 | 767 | 32 | 95 |
| 7A2 | 3 | 33 | 120 | 1060 | 31 | 99 |
| 7A3 | 5 | 38 | 60 | 1258 | 32 | 95 |
| 7A4 | 8 | 38 | 60 | 1830 | 36 | 95 |
| 7A5 | 15 | 38 | 60 | 1244 | 33 | 94 |

[1] All runs were conducted according to the procedure disclosed in Example II. The reaction was conducted under 700 psig ethylene. Other compounds present in the reaction were Ni(COD)$_2$, TCHP, and octanol the amounts used were the same as Example II.
[2] The molar ratio of TFAA to nickel was determined by dividing the number of molar equivalents of TFAA by the number of moles of nickel.
[3] See Note 3, Table IV.
[4] See Note 3, Table V.
[5] See Note 2, Table I.
[6] See Note 3, Table I.
[7] See Note 4, Table I.

TABLE VII-B

| Run[1] | Reaction Solution[2] | Molar Ratio of TFAA to Nickel[3] | Reaction Temp.[4] | Reaction Time | Productivity[5] | Amount of $C_4H_8$[7] | Amount of 1-$C_{10}H_{20}$[8] |
|---|---|---|---|---|---|---|---|
| 7B1A | Octanol | 1 | 37 | 120 | 767 | 32 | 95 |
| 7B1B | Octanol | 3 | 33 | 120 | 1060 | 31 | 99 |
| 7B1C | Octanol | 5 | 38 | 120 | 1258 | 32 | 95 |
| 7B1D | Octanol | 8 | 38 | 60 | 1830 | 36 | 95 |
| 7B1E | Octanol | 12 | 38 | 60 | 2054 | 33 | 96 |
| 7B1F | Octanol | 15 | 38 | 60 | 1244 | 33 | |
| 7B1G | Octanol | 25 | 38 | 60 | 2191 | 32 | 96 |
| 7B2A | Hexanol | 1 | 36 | 120 | 600 | 35 | 98 |
| 2B2B | Hexanol | 2 | 37 | 120 | 840 | 34 | 96 |
| 7B2C | Hexanol | 3 | 36 | 120 | 1085 | 36 | 95 |
| 7B2D | Hexanol | 5 | 38 | 120 | 1470 | 35 | 95 |
| 7B2E | Hexanol | 12 | 38 | 120 | 1622 | 34 | 96 |
| 7B2F | Hexanol | 15 | 39 | 120 | 1727 | 34 | 95 |
| 7B2G | Hexanol | 25 | 39 | 120 | 1754 | 35 | 95 |
| 7B3A | Butanol | 1 | 38 | 120 | 973 | 40 | 96 |

TABLE VII-B-continued

| Run[1] | Reaction Solution[2] | Molar Ratio of TFAA to Nickel[3] | Reaction Temp.[4] | Reaction Time | Productivity[5] | Amount of $C_4H_8$[7] | Amount of 1-$C_{10}H_{20}$[8] |
|---|---|---|---|---|---|---|---|
| 7B3B | Butanol | 2 | 38 | 120 | 1186 | 42 | 93 |
| 7B3C | Butanol | 3 | 39 | 120 | 1320 | 40 | 95 |
| 7B3D | Butanol | 5 | 37 | 120 | 1622 | 38 | 94 |
| 7B3E | Butanol | 12 | 39 | 120 | 1903 | 40 | 95 |
| 7B3F | Butanol | 15 | 39 | 120 | 1951 | 38 | 94 |
| 7B3G | Butanol | 25 | 39 | 120 | 2076 | 39 | 94 |
| 7B4A | 2E1B[9] | 1 | 37 | 120 | 632 | 28 | 97 |
| 7B4B | 2E1B | 2 | 38 | 120 | 864 | 31 | 95 |
| 7B4C | 2E1B | 3 | 38 | 120 | 988 | 29 | 96 |
| 7B4D | 2E1B | 5 | 38 | 120 | 1368 | 28 | 95 |
| 7B4E | 2E1B | 12 | 39 | 120 | 1546 | 30 | 95 |
| 7B4F | 2E1B | 15 | 38 | 120 | 1585 | 29 | 94 |
| 7B4G | 2E1B | 25 | 39 | 120 | 1693 | 29 | 95 |

[1] All runs were conducted according to the procedure disclosed in Example II. The reaction was carried out under 700 psig ethylene. Other compounds present in the oligomerization were Ni(COD)$_2$, TFAA, and TCHP the amounts used were the same as Example II.
[2] See Note 1, Table I.
[3] See Note 2, Table VIIA.
[4] See Note 3, Table IV.
[5] See Note 3, Table V.
[6] See Note 2, Table I.
[7] See Note 3, Table I.
[8] See Note, 4, Table I.
[9] 2-Ethyl-1-Butanol.

The results in these Tables shows that increasing the molar ratio of TFAA to nickel increased the productivity, while having little effect on the production of $C_4H_8$ and 1-$C_{10}H_{20}$.

EXAMPLE VIII

This example illustrates another embodiment of the invention. In particular, it describes the effect of various reaction solutions on ethylene oligomerization.

TABLE VIII-A

| Run[1] | Volume Ratio[2] | Productivity[3] | Amount of 1-$C_{10}H_{20}$[4] | Amount of Cx Produced[5] | | | | | |
|---|---|---|---|---|---|---|---|---|---|
| | | | | $C_4$ | $C_6$ | $C_8$ | $C_{10}$ | $C_{12}$ | $C_{14}$ + Up |
| 8A1A | 0:100 | 2580 | 81 | 32 | 31 | 17 | 10 | 6 | 4 |
| 8A1B | 5:95 | 1240 | 93 | 29 | 27 | 20 | 13 | 7 | 4 |
| 8A1C | 10:90 | 1006 | 94 | 32 | 25 | 19 | 13 | 7 | 4 |
| 8A1D | 25:75 | 743 | 96 | 36 | 31 | 19 | 9 | 4 | 1 |
| 8A1E | 50:50 | 367 | 99 | 40 | 31 | 17 | 8 | 3 | 1 |
| 8A1F | 100:0 | 246 | 99 | 59 | 29 | 9 | 2 | 1 | 0 |
| 8A2A | 0:100 | 2580 | 81 | 32 | 31 | 17 | 10 | 6 | 4 |
| 8A2B | 5:95 | 2113 | 93 | 29 | 27 | 20 | 13 | 7 | 4 |
| 8A2C | 10:90 | 815 | 94 | 27 | 25 | 23 | 13 | 7 | 5 |
| 8A2D | 25:75 | 1078 | 93 | 26 | 27 | 20 | 13 | 8 | 6 |
| 8A2E | 50:50 | 733 | 97 | 28 | 29 | 21 | 12 | 7 | 3 |
| 8A2F | 25:75 | 495 | 97 | 34 | 32 | 19 | 9 | 4 | 2 |

[1] All runs were conducted according to the procedure disclosed in Example II. Other compounds present during the reaction were Ni(COD)$_2$, DCHP, and TFAA the amounts used were the same as Example II. The reaction was conducted under 700 psig of ethylene. The reaction time and temperature was the same as Example II.
[2] In runs 8A1A through 8A1F the reaction solution (See Note 1, Table I), was octanol:fluorobenzene. In runs 8A2A through 8A2F the reaction solution was 2-pentanol:fluorobenzene.
[3] See Note 2, Table I.
[4] See Note 4, Table I.
[5] See Note 6, Table III.

TABLE VIII-B

| Run[1] | Reaction Solution[2] | Reaction Pressure[3] | Reaction Temp.[4] | Reaction Time[5] | Productivity[6] | Amount of $C_4H_8$ | Amount of 1-$C_{10}H_{20}$ |
|---|---|---|---|---|---|---|---|
| 8B1A | Octanol | 500 | 37 | 120 | 638 | 38 | 96 |
| 8B1B | Octanol | 600 | 35 | 120 | 681 | 38 | 96 |
| 8B1C | Octanol | 700 | 37 | 120 | 767 | 32 | 95 |
| 8B1D | Octanol | 800 | 37 | 120 | 1123 | 28 | 97 |
| 8B2A | Butanol | 700 | 38 | 120 | 973 | 40 | 96 |
| 8B2B | Butanol | 800 | 37 | 120 | 890 | 26 | 96 |
| 8B3 | 2E1B[9] | 700 | 37 | 120 | 632 | 28 | 97 |
| 8B4 | Hexanol | 700 | 36 | 120 | 600 | 35 | 98 |
| 8B5 | 2-Pentanol | 800 | 39 | 180 | 890 | 23 | 93 |

TABLE VIII-B-continued

| Run[1] | Reaction Solution[2] | Reaction Pressure[3] | Reaction Temp.[4] | Reaction Time[5] | Productivity[6] | Amount of $C_4H_8$ | Amount of $1-C_{10}H_{20}$ |
|---|---|---|---|---|---|---|---|
| 8B6 | 2M2B[10] | 800 | 37 | 180 | 1122 | 21 | 92 |

[1] All runs were conducted according to the procedure disclosed in Example II. The reaction was conducted under 700 psig ethylene. Other compounds present during the reaction were Ni(COD)$_2$, TCHP, and TFAA the amounts used were the same as Example II.
[2] See Note 1, Table I.
[3] See Note 3, Table III.
[4] See Note 3, Table IV.
[5] See Note 3, Table V.
[6] See Note 2, Table I.
[7] See Note 3, Table I.
[8] See Note 4, Table I.
[9] 2-Ethyl-1-Butanol.
[10] 2-Methyl-2-Butanol.

The results in these Tables shows that decreasing the aromatic solution decreased the productivity. However, it increased the amount of $1-C_{10}H_{20}$. Additionally, 1-alcohols had higher productivity than other alcohols.

That which is claimed is:

1. An ethylene oligomerization process comprising:
   (a) contacting, in a reaction solution, an organonickel compound and a phosphine compound to form a first reaction mixture, wherein
      said nickel component, in said organonickel compound, is in the zero valence state or can undergo reduction to the zero valence state,
      the organo component in said organonickel compound, is an unsaturated organic group,
      said phosphine compound has the formula PR$_3$, wherein each R is independently selected from the group consisting of hydrogen and hydrocarbyl radicals, provided that said hydrocarbyl radical has 1 to about 20 carbon atoms, inclusive, and that any alkenyl substitution be at least 3 carbon atoms removed from the phosphorous atom and at least one R is not a hydrogen, and the molar ratio of said phosphine compound to said nickel is from about 0.01 to about 100; and thereafter
   (b) thoroughly contacting said first reaction mixture with ethylene to form a second reaction mixture, wherein the molar ratio of ethylene to nickel is from about 1 to about 100,000,000; and concurrently with step (b) or thereafter
   (c) contacting said first reaction mixture with a fluorinated organoacid, wherein said fluorinated organoacid has the formula R"COOH, wherein R" represents a C$_1$ to about C$_{20}$ fluorinated hydrocarbyl radical having at least one fluorine atom, and the molar ratio of fluorinated organoacid compound to nickel is from about 0.01 to about 1000;
   while maintaining a reaction temperature from about 0° C. to about 200° C., and a reaction pressure of about 1 to about 10,000 psig.

2. A process according to claim 1 wherein said reaction solution is selected from the group consisting of aromatic hydrocarbons, fluorinated aromatic hydrocarbons, primary alcohols, fluorinated primary alcohols, secondary alcohols, fluorinated secondary alcohols, tertiary alcohols, fluorinated tertiary alcohols, and mixtures of two or more said reaction solutions.

3. A process according to claim 1 wherein said reaction solution is selected from the group consisting of toluene, ethanol, 2-butanol, 2-methyl-1-propanol, 2-pentanol, fluorobenzene, hexanol, octanol, 2-ethyl-1-butanol, and mixtures of two or more said reaction solutions.

4. A process according to claim 1 wherein said organonickel compound is selected from the group consisting of bis(1,5-cyclooctadiene)nickel, bis(tricyclohexylphosphine)nickel, nickel tetracarbonyl, (cyclododecatriene)nickel, bis(ethylene)(dicyclohexylphosphine)nickel, tetrakis(triphenylphosphine)nickel, bis(triphenylphosphine)nickel dicarbonyl, and mixtures of two or more said organonickel compounds.

5. A process according to claim 1 wherein said organonickel compound consist of bis(1,5-cyclooctadiene)nickel.

6. A process according to claim 1 wherein said phosphine is selected from the group consisting of dicyclohexylphosphine, tricyclohexylphosphine, triethylphosphine, tributylphosphine, diethylphenylphosphine, dicyclohexylphenylphosphine, tribenzylphosphine, ortho-tolyldiphenylphosphine, di(ortho-tolyl)phenylphosphine, triisopropylphosphine, tributylphosphine, tritertbutylphosphine, phenylphosphine, diphenylphosphine, triphenylphosphine and mixtures of two or more said phosphine compounds.

7. A process according to claim 1 wherein said phosphine compound consists of dicyclohexylphosphine.

8. A process according to claim 1 wherein said phosphine compound consists of tricyclohexylphosphine.

9. A process according to claim 1 wherein said molar ratio of phosphine compound to nickel is about 0.1 to about 10.

10. A process according to claim 1 wherein said molar ratio of phosphine compound to nickel is 0.5 to 5.

11. A process according to claim 1 wherein said fluorinated organoacid compound is selected from the group consisting of trifluoroacetic acid, heptafluorobutyric acid, difluoroacetic acid, pentafluoropropionic acid, perfluoroadipic acid, trifluoromethanesulfonic acid, heptafluoroethanesulfonic acid and mixtures of two or more said fluorinated organoacid compounds.

12. A process according to claim 1 wherein said fluorinated organoacid compound consists of trifluoroacetic acid.

13. A process according to claim 1 wherein said molar ratio of fluorinated organoacid compound to nickel is from about 0.1 to about 100.

14. A process according to claim 1 wherein said molar ratio of fluorinated organoacid compound to nickel is from 0.10 to 50.

15. A process according to claim 1 wherein said reaction temperature is from about 20° C. to about 120° C.

16. A process according to claim 1 wherein said reaction temperature is from 40° C. to 100° C.

17. A process according to claim 1 wherein said reaction solution is selected from the group consisting of alcohols, fluorinated alcohols, and mixtures of two or more said reaction solutions, and said reaction pressure is from about 100 to about 8000 psig.

18. A process according to claim 1 wherein said reaction solution is selected from the group consisting of alcohols, fluorinated alcohols, and mixtures of two or more said reaction solutions, and said reaction pressure is from 200 to 5,000 psig.

19. A process according to claim 1 wherein said reaction solution is selected from the group consisting of aromatic hydrocarbons, fluorinated aromatic hydrocarbons, and mixtures of two or more said reaction solutions, and said reaction pressure is from about 400 to 1,000 psig.

20. A process according to claim 1 wherein said reaction solution is selected from the group consisting of aromatic hydrocarbons, fluorinated aromatic hydrocarbons, and mixtures of two or more said reaction solutions, and said reaction pressure is from 500 to 900 psig.

21. An ethylene oligomerization process comprising:
 (a) contacting in a reaction solution, bis(1,5-cyclooctadiene) nickel and a phosphine compound to form a first reaction mixture, wherein said phosphine compound is selected from the group consisting of dicyclohexylphosphine, tricyclohexylphosphine, and mixtures these two phosphine compounds, and the molar ratio of said phosphine compound to said nickel is from 0.5 to 5, and said reaction solution is selected from the group consisting of toluene, ethanol, 2-butanol, 2-methyl-1-propanol, 2-pentanol, fluorobenzene, hexanol, octanol, 2-ethyl-1-butanol, and mixtures of two or more said reaction solutions; and thereafter
 (b) thoroughly contacting said first reaction mixture with ethylene to form a second reaction mixture, wherein the molar ratio of ethylene to nickel is from about 1 to about 100,000,000; and concurrently with step (b) or thereafter
 (c) contacting said second reaction mixture with a fluorinated organoacid, wherein said fluorinated organoacid is selected from the group consisting of trifluoroacetic acid, heptafluorobutyric acid, difluoroacetic acid, pentafluoropropionic acid, perfluoroadipic acid, trifluoromethanesulfonic acid, heptafluoroethanesulfonic acid and mixtures of two or more said fluorinated organoacid compounds, and the molar ratio of fluorinated organoacid compound to nickel is from 0.5 to 50; and
while maintaining a reaction temperature from about 0° C. to about 200° C., and a reaction pressure of about 1 to about 10,000 psig.

* * * * *